United States Patent [19]

Nasrallah et al.

[11] Patent Number: 5,210,182
[45] Date of Patent: May 11, 1993

[54] EXTRACTION PROCESS FOR GELATIN

[75] Inventors: Maurice Nasrallah; Parviz Ghossi, both of Tarrytown; Joseph E. Spradlin, Monroe, all of N.Y.; John R. Magnifico, Stoneham, Mass.

[73] Assignee: Kraft General Foods, Inc., Northfield, Ill.

[21] Appl. No.: 836,047

[22] Filed: Feb. 12, 1992

[51] Int. Cl.$^5$ .................... C07K 3/02; C07K 15/06
[52] U.S. Cl. ................................................. 530/355
[58] Field of Search ............................ 530/355, 354

[56] References Cited

U.S. PATENT DOCUMENTS 2,024,683 12/1935 Epstein .................... 530/355
2,557,871 6/1951 Harnack et al. .......... 530/355
5,093,474 3/1992 Grossman et al. ........ 530/355

FOREIGN PATENT DOCUMENTS 323790 7/1987 European Pat. Off. ......... 530/355

OTHER PUBLICATIONS

Kirk Othmer, "Encyclopedia of Chemical Technology," third edition, vol. 11, pp. 711-715, John Wiley and Sons, New York, 1980.

Primary Examiner—Jeffrey E. Russel
Attorney, Agent, or Firm—Thomas R. Savoie

[57] ABSTRACT

Improved yield and gelatin quality is obtained by extracting conditioned collagen-containing material with water at lower temperature and shorter time conditions than previously used to remove high quality gelatin as quickly as possible. Very high quality gelatin is extracted initially. Acid conditioning yield is also improved by controlling pH between 1.5-2.0.

16 Claims, 5 Drawing Sheets

EXTRACTION PROCESS FOR GELATIN

The present invention relates to an improved process for the extraction of gelatin from collagen-bearing material and particularly relates to a process designed to increase gelatin recovery and gelatin quality. The improved product yield and quality is obtained by increasing the amount of water normally employed in the early stages of extraction and by adjusting time, temperature and pH of extraction in conjunction with mild agitation employed to wipe extracted gelatin from the surface of the collagen containing material and allow the rapid extraction of gelatin at low temperatures. Agitation should be gentle and uniform throughout the extraction tank. Conditioning loss or collagen degradation is minimized by maintaining the conditioning pH above 1.0, preferably between pH 1.5–2.0 at a temperature between 45° F. and 55° F.

BACKGROUND OF THE INVENTION

Gelatin is obtained by the partial hydrolysis of collagen, the chief protein component in skins, bones, hides, and white connective tissue of the animal body. Gelatin is produced by either acid conditioning or by alkaline or lime conditioning followed by hot water extraction of the gelatin from the collagen material Most acid treated gelatin is made from pork skins yielding grease as a byproduct which is also marketable. The process employed includes comminuting the skins (collagen material), washing the skins to remove extraneous material, treating with a 1–5% acid solution of mineral acid in water, neutralization of the skins by adjustment of the pH with a base followed by water washing and finally water extraction in 7–8 batches at increasing temperatures up to about 212° F. Each extraction is typically conducted for approximately 2–4 hours. Grease is removed from the gelatin extract which is then filtered, concentrated, chilled and dried by air on wire mesh belts. The dry gelatin is then ground and blended to specification.

Lime treated bones but also hides and skins are comminuted and placed in liming tanks for 3–16 weeks. Material is then washed from 15–30 hours to remove the with available acids. The gelatin is then extracted as in the acid conditioned process. Kirk-Othmer "Encyclopedia of Chemical Technology", Third Edition, vol. 11, pp. 711–715, John Wiley and Sons, N.Y. 1980.

In an early U.S. Pat. No. 2,557,871 a multiple cook process was compared to a single step extraction of a dried, comminuted collagen product. The comparison employed a first cook-out at a temperature of between 120° F.–150° F. for about 3–5 hours. Further "successive" cook-outs where accomplished at progressively increasing cooking times and temperatures until the last extraction was at boiling. The gelatin solution formed was removed, filtered, evaporated, dried and ground.

In example 1 of U.S. Pat. No. 2,557,871 the first cookout was made at 140° F. for four hours followed by successive cook-outs at 155° F., 170° F., 185° F. and finally 210° F. for periods of four hours each for the first four cook-outs and ten hours at the cookout for boiling temperature. The gel strength of each cook-out diminished substantially beginning at 285 bloom and being reduced to 50 bloom for the cook-out at boiling temperature. These conventional cook-outs were then compared to the one cook-out process employing the dried, comminuted collagen product. The one cook-out process was found to be superior to any one or all of the conventional cook-outs which varied with time and temperature.

In U.S. Pat. No. 2,024,683 entitled "Gelatin Product and Method of Making Same", organic acids are found to be preferable in treating pig skin to reduce the detrimental effect of low pH caused by mineral acids on the quality of the extracted gelatin.

SUMMARY OF THE PRESENT INVENTION

While multiple extractions of gelatin at relatively low temperature are known, applicants have unexpectedly discovered that not only does the average temperature during extraction adversely impact gelatin quality but also that contacting the extractable gelatin with high temperature water for even a short period of time will adversely modify the gelatin. According to prior art practice, if the initial extraction is to be conducted at a temperature of 140° F. or below, water having a temperature in excess of 180° F. was fed to the extraction vessel to contact the relatively cool (e.g. 60° F.) gelatin-containing material (i.e. conditioned skins) so that the vessel contents will equilibrate to the desired extraction temperature.

According to the present invention the initial extraction water fed to the extraction vessel is at a temperature of 140° F. or below and the vessel contents are gradually brought up to the desired extraction temperature (e.g. 120° F.) by the use of external heat, such as by passing a portion of the aqueous liquid from the vessel, through a heat exchanger and back to the vessel. Alternatively heat could be added to the extractor contents to gradually raise the temperature of the contents to the desired temperature. Operating in this manner the extractable gelatin is never in contact with aqueous liquid having a temperature above 140° F. before being subjected to low temperature extraction, thus even localized gelatin modification is avoided. After the initial low temperature extraction, the skins will be at an elevated temperature, typically at least about 120° F., and subsequent extractions can begin by feeding water which is at or only slightly above the desired extraction temperature.

Applicants have also found that gentle and uniform agitation of the vessel contents during extraction are extremely effective to improve the yield of the resulting gelatin extraction process.

We have found that an improved yield of 8–14% and increased gelatin quality (i.e., bloom) of up to 6% in the finished product can be obtained by operating in accordance with this invention making at least two extractions below 130° F. for periods of 3.5 hours or less at a water to collagen-containing material ratio of about 1.5–2.5:1 to remove increased amounts of gelatin at relatively low temperature. Several more extractions are possible with the extraction temperature maintained below 140° F. and the time of contact of the hot water with the collagen-containing material being maintained at three hours or less. We have found that the additional water added in the low-temperature extractions permits more efficient extraction and improved recovery of gelatin in a relatively short period of time. Preferably gentle agitation is employed for extractions below 140° F. to aid in wiping the gelatin from the surface of collagen-containing material. The agitation should be sufficient to remove the bulk of the gelatin from the surface without emulsifying or dispersing the oils present in the collagen-containing material.

We have further found that an additional increase in yield of about 1% may be obtained by assuring that the collagen-containing material is conditioned in a manner during which the material is not subjected to a pH of about 1.5 or below. Gradual addition of acid is one technique to prevent the pH of the conditioned material from being reduced below 1.5 during acid conditioning, especially at temperatures greater than 55° F. This can be accomplished by permitting the rapid addition of a portion of the diluted acid to lower the pH of the conditioning solution in contact with the collagen-containing material to about pH 2.0 and then either gradually bleeding of the remaining acid into the conditioner over a period of several hours or adding a small batches of the acid over time such that the pH during conditioning is maintained between pH 1.5 to 2. We have found that allowing the pH to decrease to 1.0 or below even in localized areas results in production of low-molecular weight gelatin which is subsequently lost during the washing step.

Finally we have found that the appropriate treatment of the acid-conditioned collagen-containing material is by neutralization with a suitable base to raise the pH of the aqueous fluid to a range of pH 5-8 followed by washing with water until a cook pH of from 3.2-3.8 is achieved. This step ensures that the excess free acid is removed from the skins which otherwise would be detrimental to the quality of the gelatin obtained, especially in the first two low-temperature extractions. In this manner the bulk of the good (i.e. high bloom) gelatin is removed in the first several extractions and yield is increased some 8-14%.

As used in the description of the invention, all percents and ratios are by weight and are based on the starting weight of the as-is collagen-containing material which in the case of pig skins contains about 50%. moisture.

DETAILED DESCRIPTION OF THE INVENTION

Figure 1:
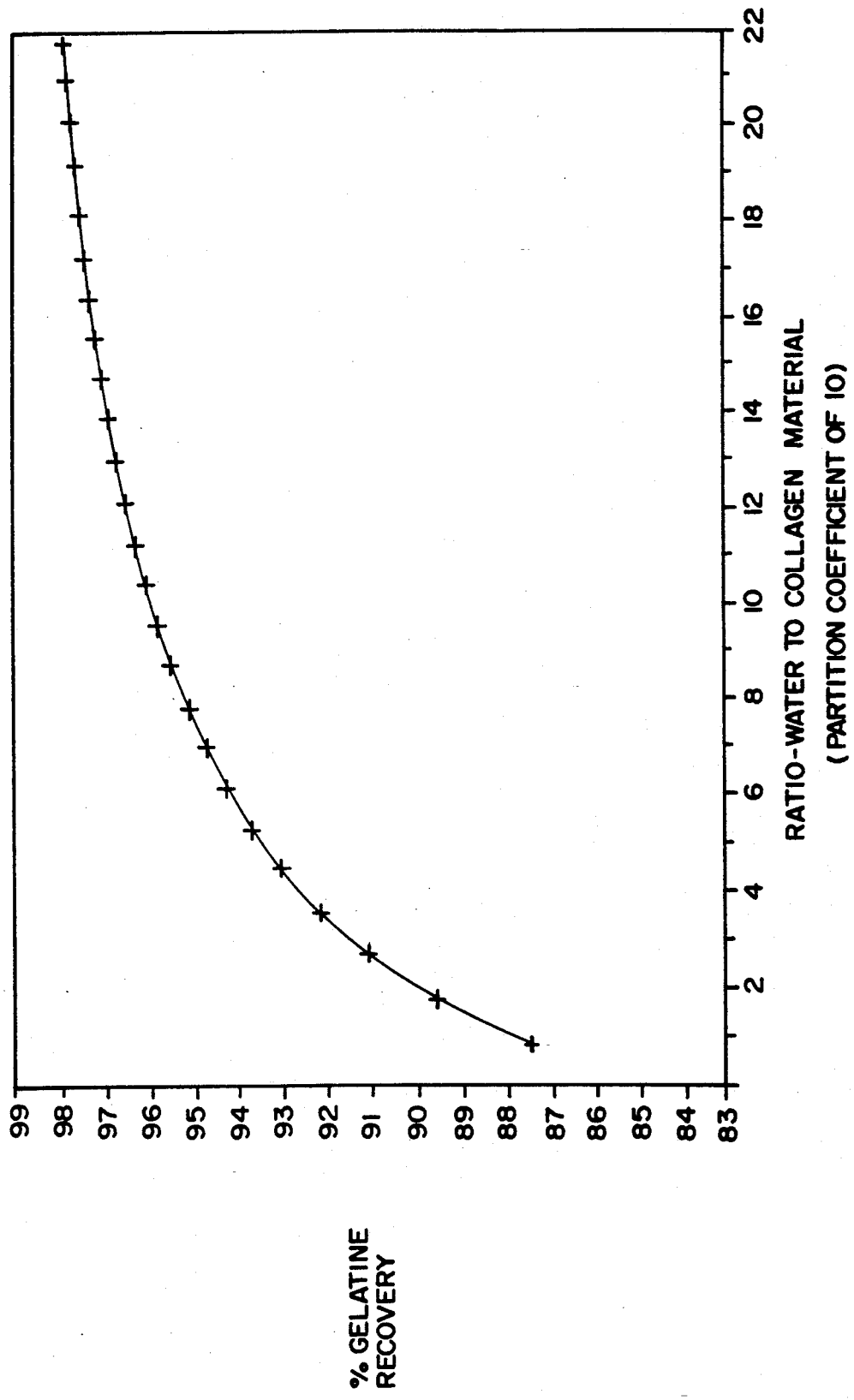
FIG. 1 is a graphic comparison of the effect of the ratio of total water used in all extraction steps to the starting weight of the collagen-containing material on the recovery of gelatin.

The process of the invention is conducted in the following manner. Collagen-containing material is contacted with an aqueous, acidic solution of a suitable mineral acid, preferably sulfuric acid, for a period of 5-7 hours at a temperature below 65° F., preferably below 60° F. The amount of sulfuric acid based on the weight of the collagen-containing material is from 2-5%.

The acid is added in a small batch of about one third of the total acid to rapidly lower the aqueous portion of the conditioning mixture to a pH about 2.0, preferably between 1.5-2.0 then allowed to equilibrate over a period of about one hour. Thereafter, the low pH is maintained by slowly adding the acid over a period of about three hours either continuously or in small batch increments. The object of this step is to avoid heavy early addition of the acid driving the pH conditioning bath in localized areas to around 1.0 or below where some collagen material is hydrolized to low-molecular weight gelatin and lost in the subsequent washing step. We have found this simple pH control step during conditioning to achieve from 1-2% improved yield of gelatin during the later extraction process. While this step is particularly useful step in the acid conditioning of collagen material where a low pH is generally produced, control of conditioning pH would also be useful in alkaline treatment where harsh bases, such as sodium hydroxide, are employed.

The acid-conditioned, collagen-containing material is next treated with an aqueous solution of ammonia or other suitable base to raise the pH of the aqueous portion of the conditioning fluid to pH 5-8, preferably about pH 7.

The collagen material is, thereafter, washed with water between 55° and 60° F. to raise the cook pH of the collagen material to between 3.0 and 4.0, preferably 3.0-3.8 and most preferably 3.2-3.5. Cook pH is determined when a sample of the conditioned collagen-containing material is cooked in boiling water and the extract pH measured. Once the proper cook pH is reached, the collagen-containing material is separated from the wash water and placed in an extractor which is then filled with warm water (up to 140° F.) to raise the batch temperature to 120° F. plus or minus 5° F. whereafter an extraction is conducted for about 2 to 4 hours using a water to collagen-containing material ratio of about 1.5-2.5:1. As noted previously it will usually be necessary to cycle a portion of the fluid from the extractor through a heat exchange to reheat to a temperature of up to 140° F. in order to achieve a batch temperature as high as 120° F. A gelatin containing extract is then removed from extractor and the remaining collagen-containing material which is then subjected to a second extraction at a water to collagen-containing material ratio of about 1.5-2.5:1 for about 1.0 to 3.5 hours at 125° F., plus or minus 5° F. Here again the water fed to the extractor is at or below 140° F., but since the collagen-containing material will already be at an elevated temperature as a result of the first extraction it may be unnecessary to cycle fluid through the heat exchange.

Further large amounts of gelatin are solubilized during the second extraction and subsequently separated from the collagen-containing material. Both the first and second extractions are preferably carried out under conditions of gentle agitation to help the water contact all surfaces of the collagen-containing material, solubilize the gelatin and carry it away from the collagen surface. Time and temperature of extractions are controlled to ensure high quality (i.e., high bloom) gelatin is recovered at surprisingly high yield. When employed, agitation is maintained uniform throughout tank. Agitation should be sufficient to force most of the skins to turn over at least once during the extraction cycle.

Agitation must, however, be kept below the point at which an emulsion is produced. The agitation is believed to increase the extraction efficiency substantially and allow large amounts of gelatin to be removed in a short period of time under extremely low temperature extraction conditions. One or more additional extractions may be conducted at temperatures at or below 140° F. for periods of up to two hours each to further remove high-quality gelatin. A water to collagen-containing material ratio of greater than about 0.6:1 is employed for each of such extractions with a preferred ratio of from 0.8-1.2:1 parts water to collagen-containing material.

After the low-temperature extractions are completed one or more extractions are made above 140° F., for typically less than two hours each at water ratios of 0.5-1.5:1. There is usually a final extraction at or about boiling temperature. These higher temperature extractions may also be made with agitation although agitation is less important.

The extracts containing quality gelatin obtained from the low-temperature (140° F. or below) extractions are generally mixed, concentrated, solidified and dried in air to a solid material which is ground and sized for commercial products. In a like manner the high-temperature (above 140° F.) extracts are similarly recovered, mixed, concentrated, solidified and dried followed by grinding and sizing. These two dried materials can then be blended to produce any bloom quality gelatin product the customer may desire.

We have found that washing the conditioned collagen-containing material before the extraction process is begun should continue until the cook pH is 3.0 to 4.0, preferably form pH 3.0-3.8 and most preferably pH 3.2-3.5. When conditioned to this cook pH, the gelatin can easily be removed at high yield and with improved quality during the first two low temperature extractions.

In extracting, we prefer to make at least four extractions and as many as ten. The first extraction is carried out at a temperature below 140° F., preferably below 130° F. for about three hours using a water to collagen-containing material ratio of 1-2.5:1, preferably 1.5-2.5:1 and most preferably 1.5-2.0:1. We prefer to make our first extraction at a temperature of 110° F.-130° F., preferably 115° F.-125° F. for 2-3.5 hours.

Our second extraction is also made below 140° F., preferably from 115° F.-135° F. and most preferably 120° F.-130° F. for 1-3.5 hours at a water to collagen-containing material ratio of 1.5-2.5:1.

Our first and second extractions are preferably made using mild agitation of 1-10 revolutions of the agitator per minute and sufficient to remove extracted gelatin from the collagen but gentle enough to avoid emulsification or dispersion of oil in the gelatin.

Later extractions are made at temperatures above 140° F. with one made at 145° F.-165° F. at a water to collagen-containing material ratio of 0.5-1.5:1, preferably about 1:1 for 1-3 hours and a final extraction at boiling, 200° F.-220° F. at a water to collagen-containing material ratio 1:1 or lower for 1-3 hours.

Usually we conduct at least two and preferably three extractions below 140° F. with the first at about 120° F. and subsequent extractions at increasing a temperature of 5° F. or more. However, several extractions can be made at the same temperatures below 140° F. since the critical factor is to agitate the conditioned collagen-containing material and quickly remove the available gelatin in order to prevent adverse modification of the gelatin during subsequent high temperature extraction.

We prefer to conduct the extractions so that our overall total water to collagen-containing material ratio for the total extraction of gelatin from the material is 8-12:1, preferably 8-10:1 and most preferably 9-10:1. The overall extraction time should be 10-20 hours, Preferably less than 16 hours.

By gentle agitation we mean simply moving the collagen-containing material to expose its surface to fresh water in order to wash away the gelatin from the surface of the material without creating oil in water dispersions or emulsions. We have found, for instance, from 3-9 RPM, of a 12 foot agitator blade in a 13 foot diameter extractor is sufficient.

While we prefer to employ gentle agitation during at least the first two extractions of the collagen-containing material, this is not necessary in order to obtain some improved yield and to recover higher quality gelatin compared to the standard process. Improvements in yield and quality is possible by simply extracting the gelatin using two first extractions below 140° F. in the manner previously described (i.e., avoiding even localized contact of the skins with water above 140° F.) each for periods of 3.5 hours or less using a water to collagen-containing material ratio of 1.5:1 or greater, thereby removing as much gelatin as possible at as mild a condition of temperature of possible. The relatively high ratio of water to collagen-containing material assists in removing gelatin from the surface of the conditioned collagen-containing material so that both yield and quality of the recovered gelatin is improved; however, although agitation does give a more effective separation and even more striking improvement in yield and quality.

In our preferred gelatin recovery process of improved yield, we take collagen-containing material and comminute it in a Reitz™ mill, or any other suitable mill, to reduce its size to about 25-100 square inches. Preferably, we reduce the collagen-containing material to a size where, on average, the pieces do not exceed about fifty square inches. We then allow the conditioning fluid (55°-60° F.) to contact and swell the material and prepare the collagen-containing material for gelatin extraction. For example, we treat the comminuted material with about 2.5% sulfuric acid by weight of the comminuted material. Thereafter, we neutralize the condition material with a suitable base such as a 1% solution of ammonia in water to achieve a pH in the aqueous phase of from 5-8. Thereafter, we wash the collagen-containing material with water (55°-° F.) to remove salts and other impurities until reaching a cooked pH of 4.0, preferably 3.0-3.8, most preferably 3.2-3.5. We then extract the collagen-containing matter using a series of separate water extractions of increasing temperature under conditions of gentle agitation. At least the first two extractions, preferably the first 3 extractions are made below 140° F. each for periods of time of 3.5 hours or less at a water to collagen-containing material ration of 1.5-2.5:1 for each extraction. These first extractions are employed to remove as much gelatin as possible at as mild temperature as possible. The mild extractions are then followed by a series of several extractions at higher temperatures at above 140° F. for 1-2 hours each using a water to initial collagen-containing material ratio of 0.5-1.5:1. These extractions are followed by a final simmer at 200° F.-220° F. for about two hours at a water to initial collagen-containing material ratio of less than 1.

The total water to the initial collagen-containing material ratio in all the extractions is maintained at 8–12:1, preferably about 9.0–10.0:1. The total extraction time of all the extractions is usually 10–20 hours, preferably about 16 hours or less.

The invention will be more fully understood from the following detailed examples which illustrate the method of treating and extracting collagen-containing material to improve the yield and quality of the resulting gelatin. It is understood that the invention is not to be restricted by the details of these examples.

EXAMPLE 1

27,000 pounds of pig skins, a collagen-containing material, is comminuted in a Reitz mill to an average size of fifty square inches and placed in a vat with sufficient water to cover the skins. The skins are treated with about 0.8% of their weight of concentrated sulfuric acid to lower the conditioning bath pH to below 2.0. About 1.5% by weight concentrated sulfuric acid based on the weight of the skins is then blended into the conditioning bath over a period of up to four hours either continuously or in small batches designed to maintain the pH at from about 1.5 to 2.0. A total from 1.5–2.5% sulfuric acid is used based on the as is weight of the skins. After some 5–10 hours conditioning at pH 1.5–2.0 the aqueous batch is neutralized with 1% aqueous ammonia and the conditioned skins are then washed with water to remove salt and extraneous matter and to obtain a cook pH of 4.0 or lower, preferably 3.0–3.5. The water temperature is maintained below 60° F., preferably below 55° F. during the entire conditioning and wash process.

The cook pH is determined by removing a sample of the collagen-containing material and cooking in about an equal weight of added water, for one hour and then measuring the filtered aqueous solution pH.

After conditioning, the skins are transferred to an extractor fitted with a simple mixer and with temperature control. Warm water not exceeding 140° F. is added and external heat is supplied to gradually raise the temperature of the extractor contents to 120° F. where the skins are extracted with gentle agitation for three hours using a 1.6:1 water to skins ratio. The gelatin-containing solution is drained off and fresh warm water added, with heating as necessary, to bring the temperature of the extractor contents to 125° F. The skins are now extracted at 125° F. for two hours at a 2:1 water to skins ratio again using gentle agitation. The gelatin solution is again drained. This procedure is followed for a series of eight extractions in total, each made as follows:

| Extraction | Time Hrs | Temperature °F. | Water to Skins Ratio (based on 27,000 lbs. of skins) |
| --- | --- | --- | --- |
| 1 | 3 | 120 | 1.6 |
| 2 | 2 | 125 | 2.0 |
| 3 | 2 | 130 | 1.2 |
| 4 | 2 | 135 | 1.2 |
| 5 | 2 | 140 | 1.0 |
| 6 | 1.5 | 150 | 1.0 |
| 7 | 1.5 | 160 | 0.5 |
| 8 | 2 | 212 | 0.5 |
| Totals | 16 | | 9.0 |

The yield of gelatin from the process of example 1 compared to the conventional process is as follows:

TABLE 1

| | Extraction Recovery | | Improved Recovery |
| --- | --- | --- | --- |
| | Invention | Standard | |
| Select Skins | 88% | 72.0% | 16.0% |
| Lower Grade Skins | 75% | 62.5% | 12.5% |

In addition to improved recovery, the quality of the gelatin recovered by the process of the invention was higher (about 6%) than with the standard extraction process.

The effect of the ratio of water to collagen-containing material wa investigated and the results set forth in FIG. 1. Increasing amounts of water was found to have a pronounced effect on the recovery of gelatin with a total ration of 8–12:1 parts water to the as is weight of the collagen-containing material preferred for best recovery of high grade gelatin at high yield without excessive dilution of the gelatin necessitating high concentration costs.

Figure 2:
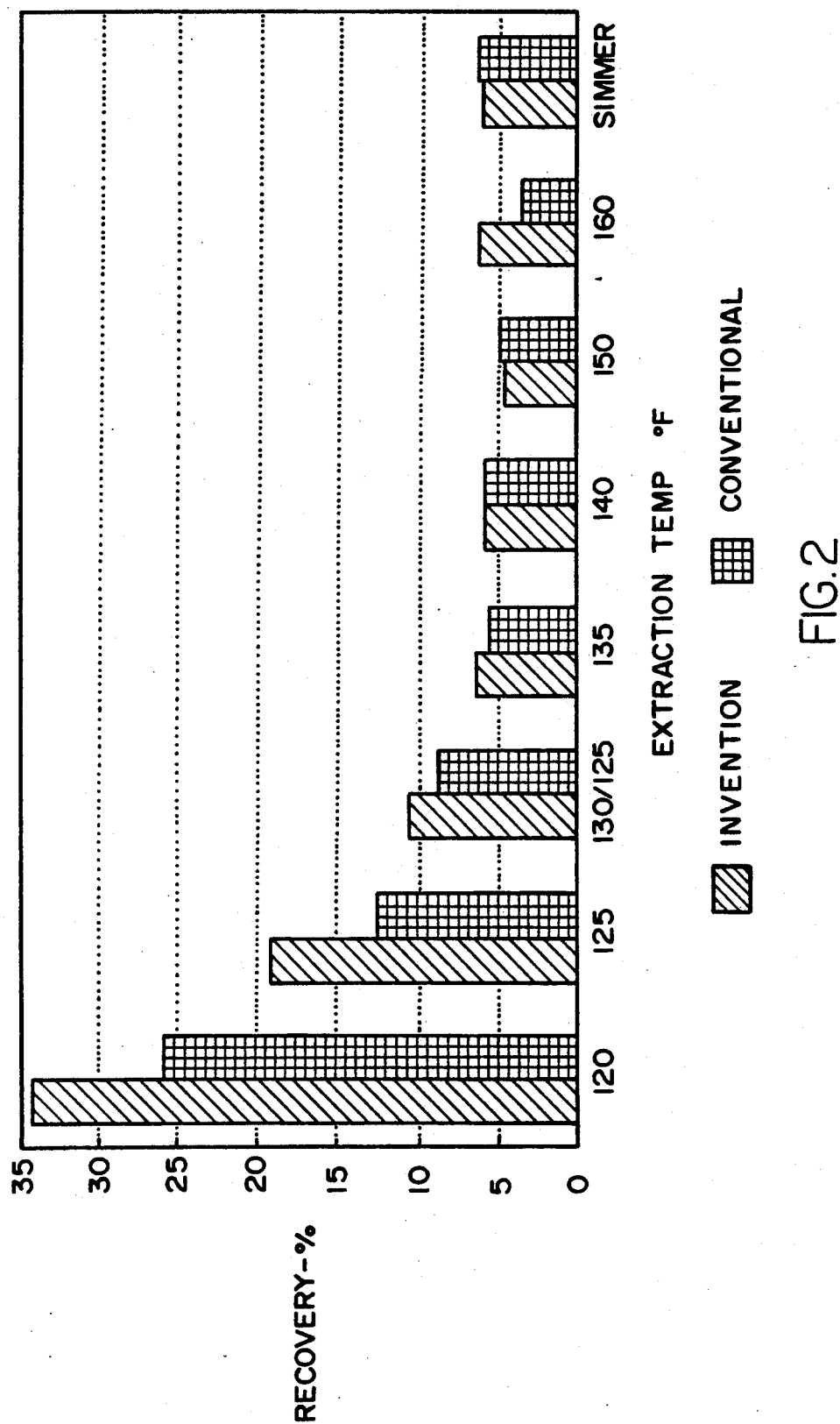
FIG. 2 is a bar graph comparing the recovery of gelatin extracted conventionally (no agitation) to the process of this invention (with agitation, as well as time, temperature and pH control) at various sequential extraction temperatures.

In FIG. 2 the recovery of gelatin from extractions made in a manner set forth in example 1 is compared to conventional extraction which employ lower (about 5–7) water to collagen containing material ratios and no agitation. As can be seen, the bulk of the yield increase is accomplished in the first two extractions made below 130° F.

The agitation employed in this invention removes the gelatin from the skin surface and allows faster and greater extraction of solids as is shown by 8% absolute and 6.5% absolute increase in gelatin recovered during the first two extraction. Adverse modification of the gelatin is minimized by maintaining mild agitation of the collagen material and extraction times of three hours or less wit the water to collagen-containing material ratio maintained at 1.5:1 or higher.

Figure 3:
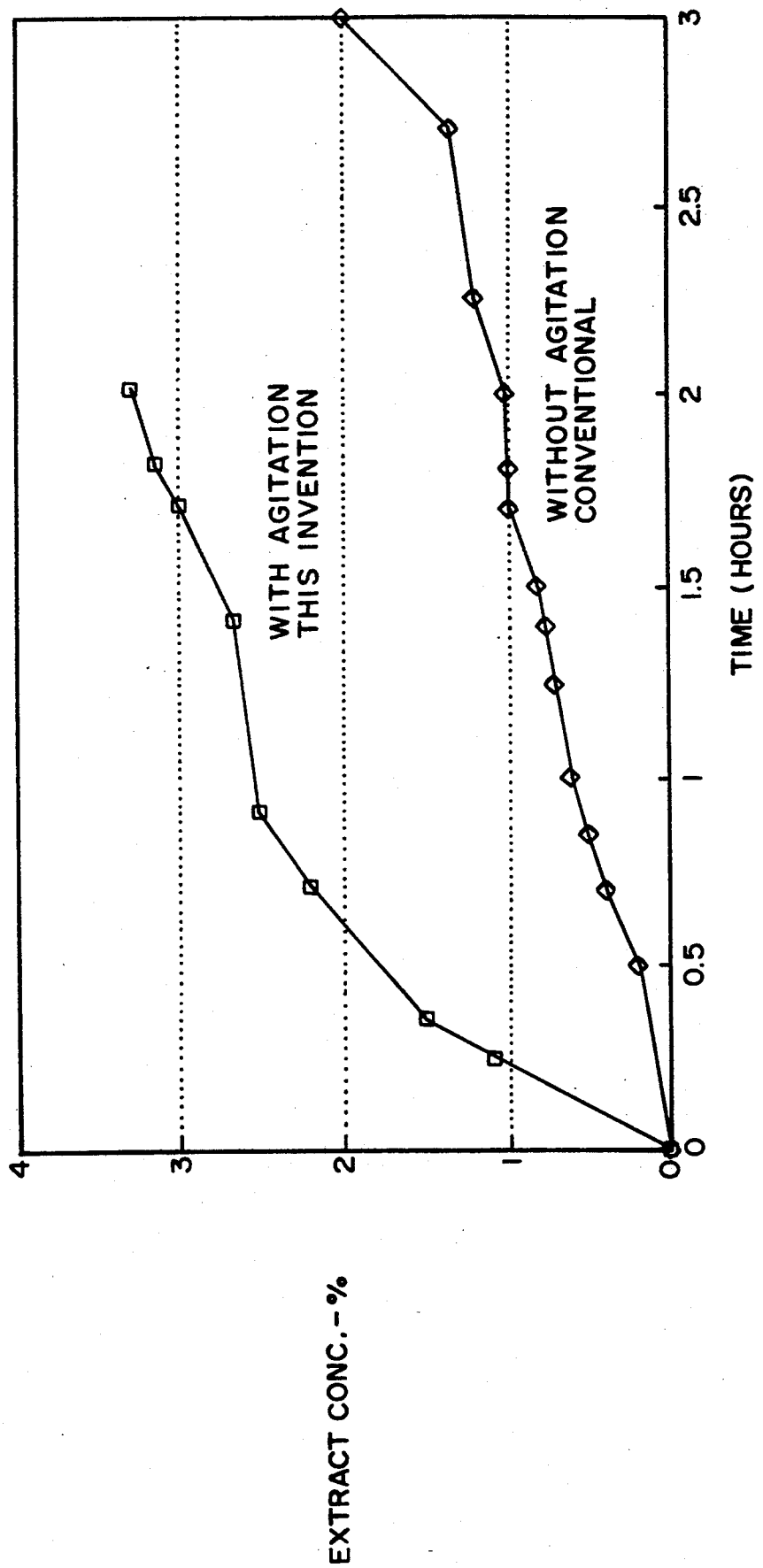
FIG. 3 is a graphic comparison of the effect of agitation during extraction as practiced in this invention compared to the prior art extraction without agitation.

FIG. 3 is a plot of gelatin concentration against extraction time, with and without agitation, for an extraction conducted in accordance with example 1. As can be readily seen, mild agitation of the collagen material results in reaching a 2% concentration in about two-thirds of an hour compared to three hours extraction time required without agitation. This improved extraction of gelatin allows removal of quality gelatin with minimum degradation caused by time-temperature conditions.

Figure 4:
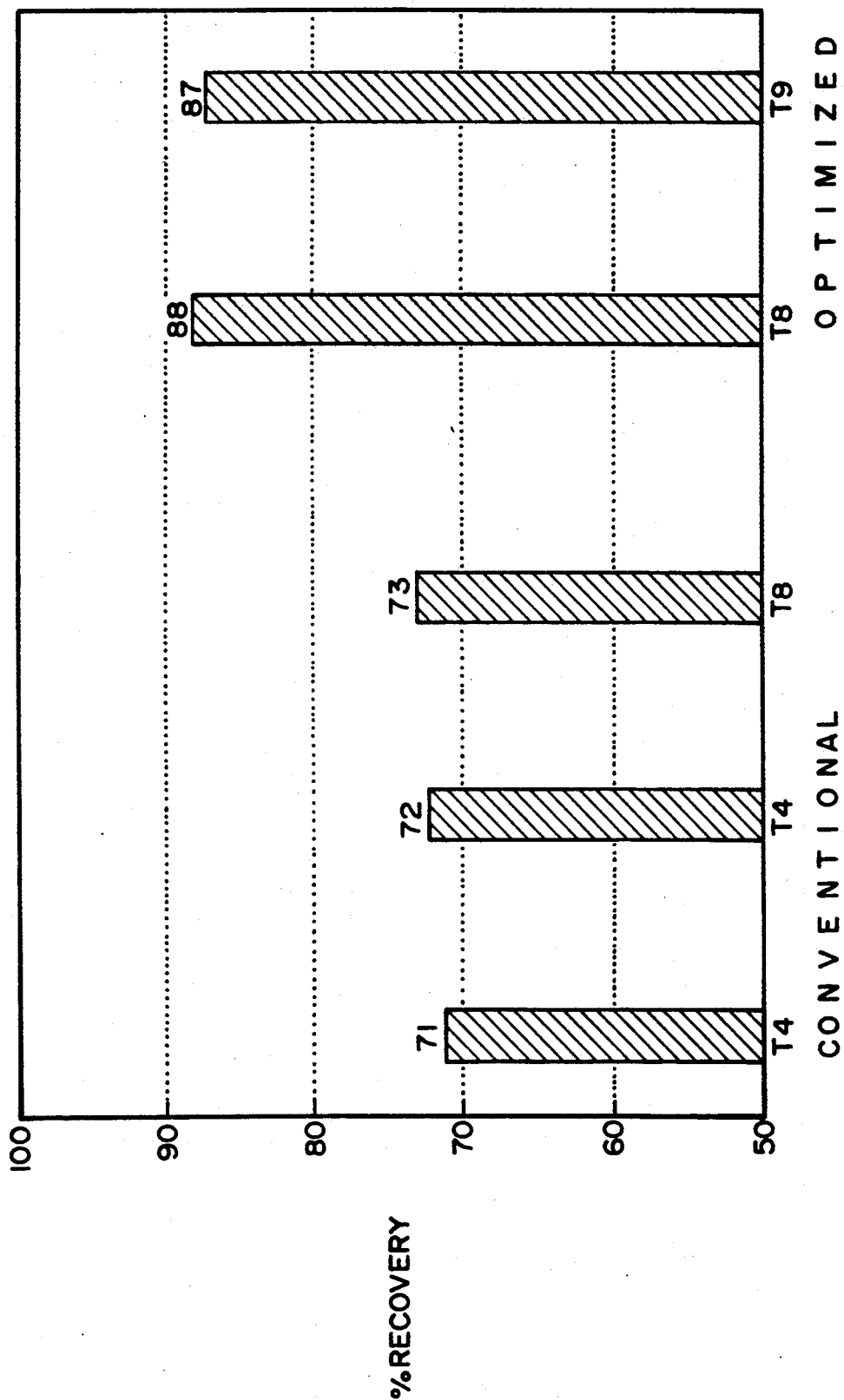
FIG. 4 is a graphic comparison of the effect of agitation and pH on recovery of gelatin, with T4, T8 and T9 indicating various experiments.

FIG. 4 illustrate the improvement in recovery of gelatin produced by use of moderate agitation of the collagen material during extraction at a pH of 3.3 and within the preferred range of 3.2 to 3.5. While some improvement in yield is obtained by short-time, low-temperature extraction following the process conditions in example 1 without agitation, it is the agitation which aids removal of the gelatin form the surface of the collagen containing skin, therefore, giving a greater extraction of gelatin at any given extraction time and temperature.

Figure 5:
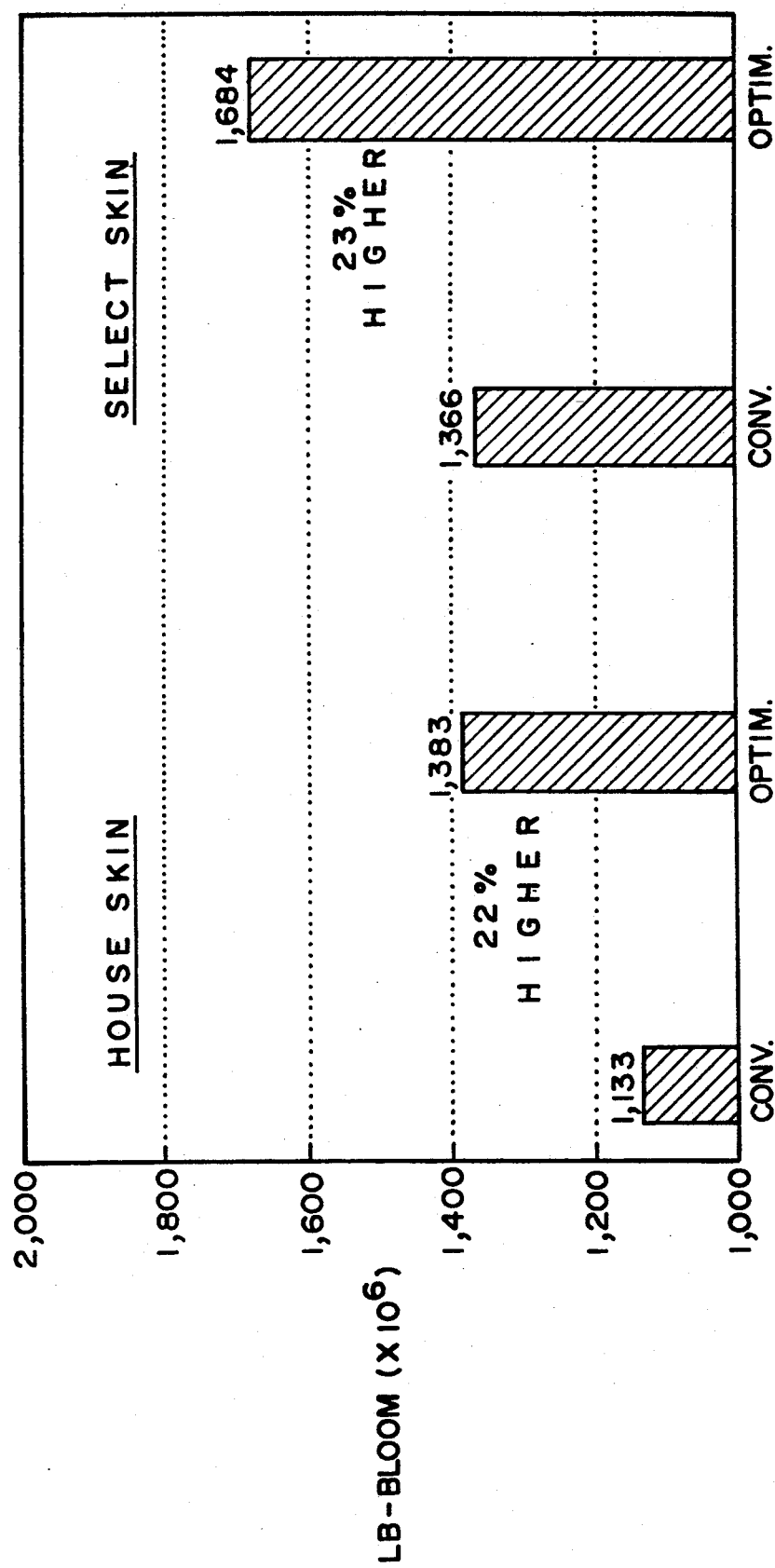
FIG. 5 is a graphic comparison of the mathematic product of yield, multiplied by bloom which is the most important economic indicator of the value of the process of this invention.

FIG. 5 shows a 22-23% improvement in terms of the product of pounds of gelatin extracted multiplied by the quality (bloom) of the gelatin extracted which is a measure of the economic value of the process of this invention in lbs.-bloom. Results of extracting both high grade and low grade collagen material are shown and each was extracted as set forth in example 1. The conditions of low temperature and time with mild agitation remove a higher yield of high quality gelatin having improved gel strength characteristics.

In making the numerous gelatin extractions which require a total of several hours extraction time, it is first necessary to add water to the collagen-containing material which normally takes one-half hour, and to thereafter heat the resulting mixture to the desired extraction temperature which normally takes twelve minutes except for the first extraction temperature which requires one half hour t being the cold skins to the extraction temperature. Following extraction the gelatin solution is drained from the collagen material over a 30 minute period. These times are not included in the extraction time.

TABLE 2

| Effect of Manner of Adding Conditioning Agent on Yield | | |
|---|---|---|
| Yield Loss (Incrementally Acid added) | Yield Loss (Acid added at one time) | Reduced Loss of Yield |
| 6.7% | 7.8% | 1.1% |
| 4.1% | 5.3% | 1.2% |

In conditioning the skins we have found that the addition of the mineral acid should be made gradually to maintain the pH between 1.5 and 2.0. When added as one batch at the beginning of conditioning the pH of the conditioning liquid is initially is lowered to around pH 1 which causes an added 1% or more loss of yield as is shown in Table 2. While this yield improvement is not as dramatic as achieved by short-time, low-temperature extraction with agitation of the collagen-containing material, it does represent an improvement that can readily be accomplished in any gelatin plant.

EXAMPLE 2

The procedure followed in example 1 is repeated using the processing conditions which follow. Mild agitation was employed in example 2I but not in example 2S.

A comparison of the process of this invention (example 2I) with the standard process (example 2S) illustrates the advantages of this invention. Much more high grade gelatin is collected at low extraction temperature which gives an overall improvement in Bloom and Viscosity. In addition, the recovery of high grade gelatin and overall process yield is much better.

What is claimed is:

1. A gelatin recovery process of improved gelatin quality and yield comprising the steps of:
   (a) conditioning comminuted collagen-containing material with acid over a period of time to swell the material and prepare it for gelatin extraction;
   (b) thereafter adjusting the acid-treated collagen-containing material in water to a water phase pH of from 5-8;
   (c) washing the pH-adjusted collagen-containing material to remove salt and other impurities until there is reached a cook pH of below 4.0;
   (d) thereafter extracting the collagen-containing material in a series of separate water extractions, wherein at least the first two extractions are made below 140° F., for periods of time of 3.5 hours or less and at a water to collagen-containing material weight ratio of equal or greater than 1.5:1 and wherein the collagen-containing material does not come into contact with any water having a temperature above 140° F.;
   (e) recovering the gelatin extracts in one or more batches;
   (f) concentrating the gelatin extracts;
   (g) solidifying and drying the gelatin; and
   (h) grinding the dried gelatin to give a quality gelatin product.

2. The process of claim 1 wherein gelatin extraction is conducted under conditions of mild agitation in a series of from four to ten extractions and wherein the overall water to collagen containing material weight ratio is from 8-12:1.

3. The process of claim 2 wherein each of the initial water extractions are made at a temperature of 110° F. to 130° F., for a time of 2-4 hours and at a water to collagen-containing material weight ratio of from 1.5-2.5:1 and wherein the collagen material has a cook pH of 3.0 or greater.

4. The process of claim 3 wherein the initial water extraction is at about, 120° F. for a time of up to three hours.

5. The process of claim 1 wherein there are at least three water extraction stages which are followed by a simmer step, with the initial water extraction being at about 110° F.-130° F., with a subsequent extraction conducted at or below 140° F., and with a final high temperature extraction above 145° F. and wherein the cook pH of the collagen material is pH 3.0-3.8.

6. The process of claim 5 wherein the duration of the first two water extractions are each longer than that of the last water extraction.

7. The process of claim 5 wherein total water to original collagen-containing material weight ratio, is about 8.0-10.0:1.

8. The process of claim 1 wherein the initial extraction is made for a time of 2-3.5 hours and subsequent extractions are made for a time of from 1 hour to less than 2.5 hours each such that the total extraction time is less than 20 hours.

9. The process of claim 1 wherein the water to collagen-containing material weight ratio in the third and subsequent extractions is less than or equal to the water ratio in the first and second extractions.

10. The process of claim 1 wherein the collagen-containing material is agitated and the agitation during extraction is sufficient to remove gelatin from the surface of the collagen material 11. The process of claim 10 wherein agitation is effected by an agitator at 3 to 9 RPM's.

12. The process of claim 1 wherein the pH of the gelatin extracts are 3.0 to 4.0.

13. The process of claim 5 wherein the water extractions are at least as follows: a first extraction under mild agitation at from 110° F.-130° F. for about 2-4 hours at a water to collagen-containing material weight ratio of about 1.5-2.5:1; a second extraction under mild agitation at from 115° F.-140° F. for up to four hours at a water to collagen-containing material weight ratio of about 1.5–2.5:1, at least one extraction at from 145° F.–165° F. for 1–3 hours at a water to collagen-containing material weight ratio of about 0.5–1.5:1 and a final simmer at 200° F.–220° F. for about 1–3 hours at a water to collagen-containing material weight ratio of less than 1.5, said conditions maintained such that the total water to collagen-containing material weight ratio is maintained at 8–12:1 and the total extraction time is about 16 hours or less.

14. The process of claim 1 in which the conditioning step is conducted using sulfuric acid at a water to collagen-containing material weight ratio of about 2:1 and wherein once a portion of acid is added to lower the pH to below 2.0, the remaining acid is next added step-wise or continuously over several hours to maintain the pH in the aqueous phase at about 1.5–2.0 and prevent the pH of the skin from becoming excessively acid and causing loss of gelatin.

15. The process of claim 14 in which the water temperature is maintained below 60° F. during conditioning.

16. The process of claim 15 in which the collagen acid treated material is neutralized with an equivalent amount of base to a pH of 5–8 and then washed with water to a cook pH of 3 to 4.

* * * * *